(12) United States Patent
Betts

(10) Patent No.: US 8,157,804 B2
(45) Date of Patent: Apr. 17, 2012

(54) EXPANDABLE BLADE DEVICE FOR STABILIZING LONG BONE FRACTURES

(75) Inventor: Andres Betts, San Clemente, CA (US)

(73) Assignee: Vertech, Inc., San Clemente, CA (US)

( * ) Notice: Subject to any disclaimer, the term of this patent is extended or adjusted under 35 U.S.C. 154(b) by 739 days.

(21) Appl. No.: 11/836,720

(22) Filed: Aug. 9, 2007

(65) Prior Publication Data

US 2008/0221575 A1    Sep. 11, 2008

Related U.S. Application Data

(60) Provisional application No. 60/893,556, filed on Mar. 7, 2007.

(51) Int. Cl.
*A61B 17/00* (2006.01)
*A61B 17/58* (2006.01)
*A61B 17/60* (2006.01)
*A61F 2/46* (2006.01)
*A61F 2/00* (2006.01)

(52) U.S. Cl. ............ 606/79; 606/86 R; 606/95

(58) Field of Classification Search .......... 606/79, 606/80, 86 R, 95
See application file for complete search history.

(56) References Cited

U.S. PATENT DOCUMENTS

| 5,591,170 A * | 1/1997 | Spievack et al. ............ 606/82 |
| 5,697,932 A * | 12/1997 | Smith et al. ............ 606/80 |
| 2007/0156225 A1 * | 7/2007 | George et al. ............ 623/1.12 |

* cited by examiner

*Primary Examiner* — Thomas C. Barrett
*Assistant Examiner* — David Bates
(74) *Attorney, Agent, or Firm* — Fish & Associates, PC

(57) ABSTRACT

The present invention relates generally to medical devices and medical methods, in particular, devices and methods useful for stabilizing fractures of long bones. In one embodiment, the present invention is a device comprising a housing having a lumen; a plunger having a proximal portion and a distal portion, where the plunger is disposed within the lumen and is movable relative to the housing; a plurality of blades, where the blades can expand radially from the axis of the housing; and a manipulator functionally connected to the plunger, wherein the manipulator is operable to: move the plunger relative to the housing; expand the blades radially from the axis of the housing; and move the blades about the axis of the plunger.

10 Claims, 9 Drawing Sheets

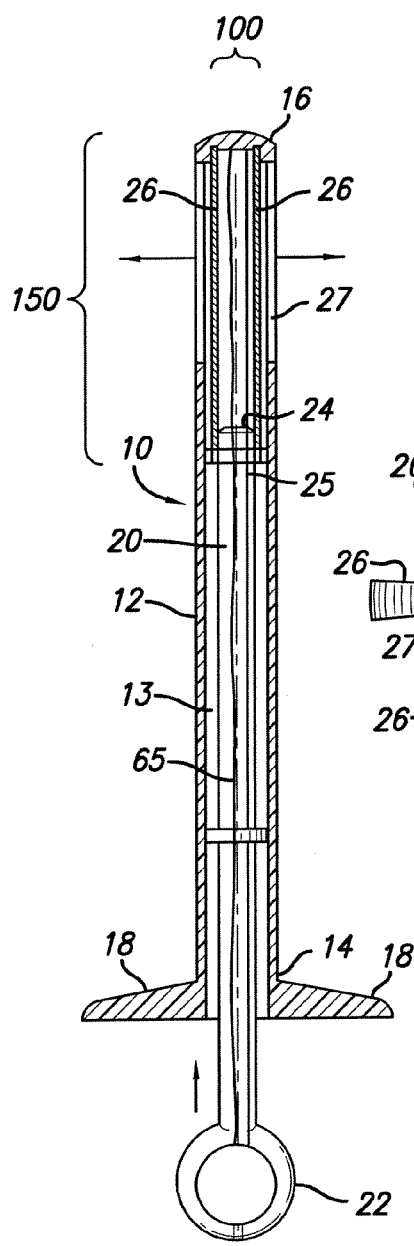
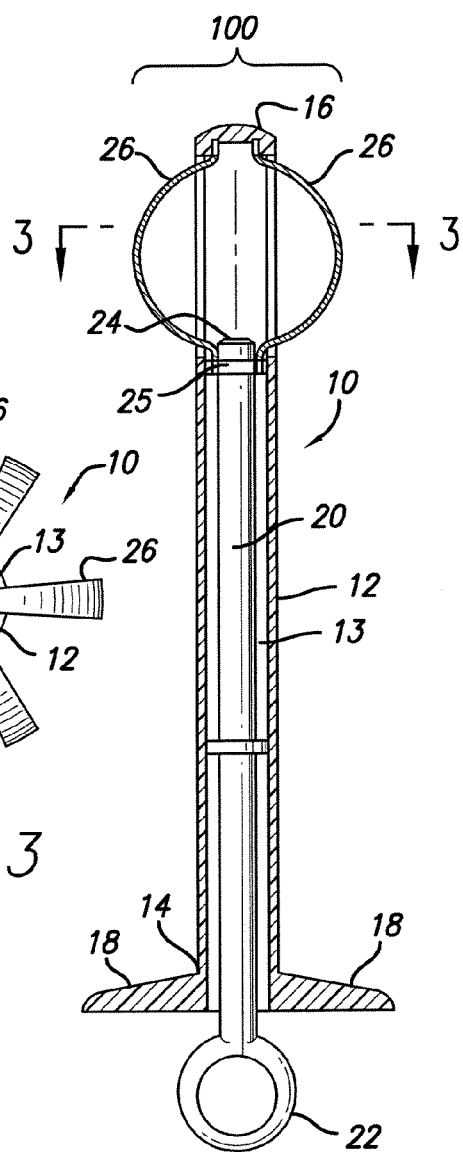
FIG. 1
FIG. 3
FIG. 2

__US 8,157,804 B2__

EXPANDABLE BLADE DEVICE FOR STABILIZING LONG BONE FRACTURES

CROSS-REFERENCE TO RELATED APPLICATION

This application claims priority to provisional patent application Ser. No. 60/893,556, filed on Mar. 7, 2007, which is hereby incorporated by reference in its entirety.

FIELD OF THE INVENTION

The present invention relates generally to medical devices and medical methods. More particularly, the present invention relates to devices and methods useful for stabilizing fractures of long bones.

BACKGROUND OF THE INVENTION

The treatment of long bone fractures typically involves the open reduction and internal fixation of the fracture using complex plate and screw systems, or the insertion of precisely tailored intramedullary metal rods. Such systems require an open incision and placement of metal hardware that must be specifically scaled to the size of the bone and type of fracture. The inventory of orthopedic hardware devices a given hospital must keep available is large, with a high associated cost of storage and close monitoring of availability, so as not be found lacking at the time of surgery. Moreover, in many patients with osteoporosis the weakened bone cannot support the internal fixation screws placed for open reduction with the plate and screw system. There is a significant risk of the screws to pull free from the osteoporotic bone with loss of the fracture reduction.

SUMMARY OF THE INVENTION

The present invention relates to devices and methods useful for stabilizing fractures of long bones. More particularly, the present invention relates to devices utilizing a plurality of expandable blades and methods of using such devices.

In one embodiment, the present invention is a device comprising a housing having a lumen; a plunger having a proximal portion and a distal portion, where the plunger is disposed within the lumen and is movable relative to the housing; a plurality of blades located at the distal portion of the plunger, where the blades are operable to: expand radially from the axis of the housing; and exert force radially; a manipulator functionally connected to the plunger, wherein the manipulator is operable to: move the plunger relative to the housing; expand the blades radially from the axis of the housing; and move the blades about the axis of the plunger. In some embodiments, the device has six blades. In other embodiments, the device has two blades. In some embodiments, force exerted on the blades is transferred to the manipulator. In certain embodiments, the plunger is flexible. In some embodiments, the blades expand to a plurality of diameters.

The methods of the present invention may be used to stabilize fractures of long bones and other hollow bones. In some embodiments, a device is used to perform an internal osteotomy of the intramedullary trabecular bone without completely reaming the marrow cavity. In one implementation, a method includes the steps of accessing the marrow cavity of a long bone; inserting a device into the marrow cavity, where the device has a variable diameter cutting element; reducing the volume of trabecular bone within the marrow cavity; instilling a biological binding material into the marrow cavity of the long bone, where the amount of the biological binding material instilled is sufficient to add stability to the long bone.

In some embodiments the accessing step uses a percutaneous method. The variable diameter cutting element may comprise a plurality of blades. In some embodiments the reducing step includes manipulating the plurality of blades to cut trabecular bone within the marrow cavity to create a space in the marrow cavity. In one embodiment, the biological binding material is PMM cement. In some embodiments the biological binding material interdigitates with trabecular bone in the marrow cavity. The method may further include the step of monitoring the movement of the device by fluoroscopic imaging.

In some embodiments the present invention is a kit including a device as described herein; a large-bore cannula; a PMM cement; and a device operable to deliver the PMM cement to an internal volume of a bone.

Alternatively, in certain fractures where a plate and screw system is employed in the fracture repair approach, the intramedullary PMM cement may be instilled prior to placement of plate and/or screws. When the PMM cement is allowed to harden the screws may be placed in the usual fashion but will be securely anchored into the predelivered PMM cement, rather than osteoporotic bone.

BRIEF DESCRIPTION OF THE DRAWINGS

FIG. 1 is a partial cross-sectional view of an embodiment of a device of the present invention with its blades in a retracted position.

FIG. 2 is a partial cross-sectional view of the embodiment depicted in FIG. 1.

FIG. 3 is a top-down view of the embodiment depicted in FIG. 2.

DETAILED DESCRIPTION

Figure 4:
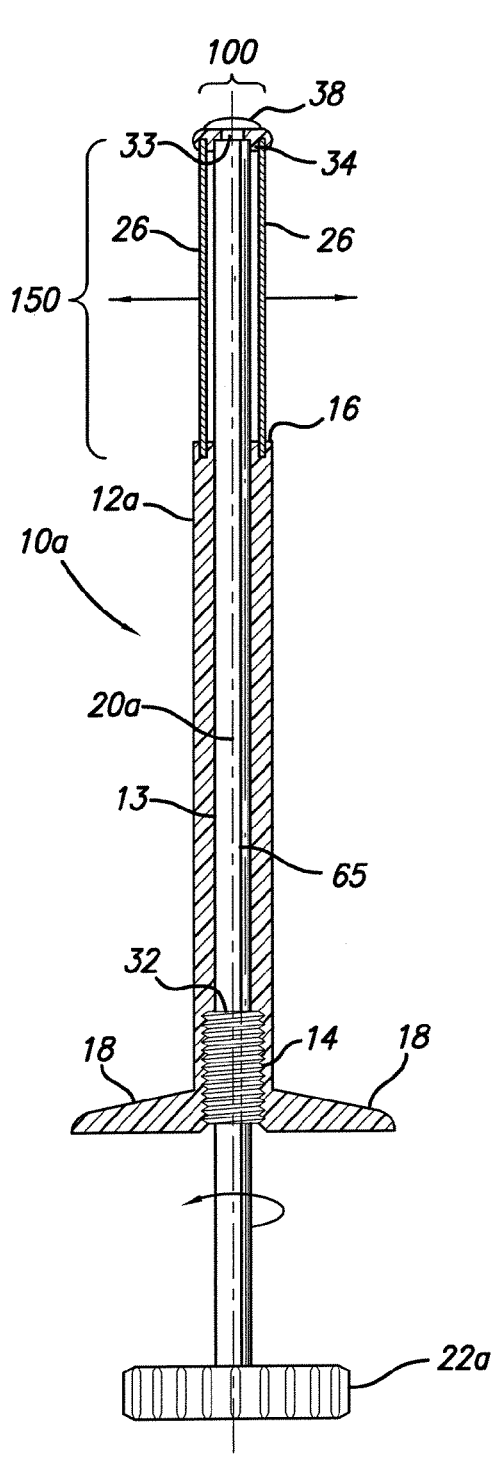
FIG. 4 is a partial cross-sectional view of an embodiment of a device of the present invention.

In the following paragraphs, the present invention will be described in detail by way of example with reference to the attached figures. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

A. Devices of the Present Invention

Referring now to the figures, which are illustrative of multiple embodiments of the present invention only and are not for purposes of limiting the same, FIG. 1 depicts an expandable blade device 10 constructed in accordance with one embodiment of the present invention. The expansion blade device includes a rigid housing 12 which defines a lumen 13. Preferably the housing 12 is roughly tubular, but it may be any suitable shape or configuration. Housing 12 may be any suitable material, such as a suitable polymer, plastic, metal or alloy. In some embodiments, housing 12 may be flexible.

Housing 12 may have a length of about 15 cm. The lumen 13 is preferably tubular, but it may be any suitable shape or configuration. In preferred embodiments, the device 10 of the present invention is insertable within a cannula 60 which has been placed within the injured long bone. Preferably, cannula 60 is a large bore cannula between about eight gauge to about eleven gauge.

The housing 12 has a proximal end 14 and a distal end 16. Preferably, distal end 16 is closed. In some embodiments, proximal end 14 includes grip member 18 that may aid a user's ability to grip and/or manipulate device 10. In some embodiments, grip member 18 is located at proximal end 14, but grip member 18 may be located near proximal end 14 or at any suitable position on housing 12. In the depicted embodiment, grip member 18 is a pair of wings where each wing extends outwardly from proximal end 14 in opposed relation to the other. In such an embodiment, a user's index finger may be placed over one of the wings comprising grip member 18, while the user's middle finger may be placed over the other wing comprising grip member 18, similar to the handling of a syringe. In other embodiments, grip member 18 may be any suitable structure that may aid user's ability to grip and/or manipulate device 10, for example finger loops, depressions, grooves, or a textured surface.

As illustrated in FIGS. 1 and 2, plunger 20 is disposed within the lumen 13 of housing 12 such that plunger 20 is movable relative to housing 12. Similar to housing 12 and lumen 13, plunger 20 may be any suitable diameter and length. In preferred embodiments, plunger 20 has a diameter slightly less than lumen 13 such that plunger 20 is movable along the axis of the housing, but exhibits little, if any, movement transverse to the axis of the housing. In some embodiments, plunger 20 may be equipped with a structure or structures that facilitate its movement within the lumen 13. In some embodiments, plunger 20 may be flexible.

A manipulator 22 is located at or near the proximal end of plunger 20. Manipulator 22 may be any structure suitable to permit the user to move plunger 20 relative to housing 12. In some embodiments manipulator 22 may be a loop, a lever, handle, or dial. In preferred embodiments, manipulator 22 is connected, directly or indirectly, to plunger 20 and blades 26 such that force acting upon blades 26 is transferred to manipulator 22. Accordingly, in preferred embodiments, the user of device 10 is provided with a tactile feel.

Attached to the distal portion of plunger 20 is a plurality of blades 26. The use of multiple blades, as opposed to a single blade, promotes more reliable fluoroscopic imaging in multiple planes. Each blade 26 may have any suitable width and each blade 26 in a given device need not have the same width. In some embodiments the blades 26 may have a width of from about 0.5 mm to about 10 mm. Preferably, each blade 26 has a width of from about 2 mm to about 3 mm. The blades 26 are disposed substantially parallel to the axis of housing 12 and, in their unexpanded stated, do not protrude past the outer surface of housing 12. Each blade 26 may be composed of any suitable material that can cut or shave trabecular bone and is resilient. In some embodiments, blades 26 may be made of any compliant polymer, plastic, metal or alloy. Preferably, blades 26 are made of metal. Embodiments of the invention may feature any number of blades 26. In some embodiments there may be 2, 3, 4, 5, 6, 7, 8, 9, or 10 blades. In a preferred embodiment, there are six blades 26. In another preferred embodiment, there are two blades 26.

In some embodiments, the distal portion of housing 12 has a plurality of slots 27. Preferably the slots 27 are located close to the distal end 16. The slots 27 may be any shape and size so long as they do not impede radial expansion of the blades 26. In the illustrated embodiment, the slots 27 are elongate rectangular in shape.

Blades 26 are disposed such that when manipulator 22 is moved in a certain manner, the blades 26 will expand radially from the axis of the housing. In some embodiments, this is achieved by translating the distal movement of plunger 20 along the axis of housing 12, for example as depicted in FIG. 2, in to the expansion or flexing of blades 26 radially away from the axis of the housing 12 and through slots 27. In the illustrated embodiments such movement is achieved by attaching the proximal ends of blades 26 to plunger 20 and attaching the distal ends to housing 12. Blades 26 may be attached to plunger 20 and housing 12 in any suitable manner, including indirectly. In some embodiments, blades 26 may be attached by welding, crimping, screws, rivets, or adhesives. The blades 26 may be attached to any suitable location of the plunger 20 and housing 12. Preferably, the proximal ends of blades 26 are attached in proximity to the distal end 24 of plunger 20 and the distal ends of blades 26 are attached to an interior surface of the housing 12 at the distal end 16. In a preferred embodiment, the proximal ends of blades 26 are each attached to a shoulder portion 25 of the plunger 20 which is located proximally to the distal end 24 of plunger 20.

The disposition of the blades 26 is also such that a diameter 100 of the blades 26 in the expanded configuration is variable. FIG. 1 illustrates an embodiment where blades 26 are not expanded radially outward, whereas FIG. 2 illustrates an embodiment that where the blades 26 are expanded to the maximum diameter. Although not depicted, the user may vary the extent of the expansion of the blades 26 and thereby vary the diameter 100 between the maximum and the unexpanded states. The user varies the diameter by varying the movement of the plunger 20 relative to the housing. The user may control this movement by acting upon the manipulator 22 and moving the manipulator 22 with respect to grip member 18. Accordingly, for example, in FIGS. 1 and 2 the user's movement of the manipulator 22 toward the distal end 16 of housing 12 moves plunger 20 toward the distal end 16 of housing 12. In turn, the movement of plunger 20 moves the proximal end of blade 26 toward the distal end of blade 26, thereby expanding blade 26 radially from the axis of housing 12. FIG. 3 depicts device 10 from a top-down perspective, with the blades 26 being in a fully deployed state illustrated in FIG. 2. As is illustrated in FIG. 3, each blade 26 protrudes through a slot 27 disposed within the rigid housing 12. In some such embodiments, the distance of the movement of plunger 20 toward the distal end of housing 12 controls the amount of expansion of blade 26 and the diameter 100. In a preferred embodiment, the maximum diameter between blades is about 2 cm. In some embodiments manipulator 22 is configured to display or otherwise notify the user of the cutting diameter of the blades 26. For example, manipulator 22 or the distal portion of plunger 20 may have markings showing the extent of radial expansion of blades 26 achieved by a certain movement of manipulator 22.

Due to the resiliency and shape memory properties of blades 26, once expanded, the blades have a tendency to return to their unexpanded position depicted in FIG. 1. Accordingly, in some embodiments, the blades 26 remain expanded only so long as the user applies force to the manipulator 22 (and thereby to plunger 20). In other embodiments, the manipulator 22 is configured such that the user need not apply continuous force to maintain the expansion of blades 26. In some such embodiments, the blades 26 may be maintained in a fully or partially expanded state through the use of a clamp, or some other fastening means (not shown) that is operable to maintain the plunger 20 in a prescribed position relative to the housing 12.

In some embodiments, device 10 may also have a guide wire engaging member 65 that functions to engage a structure that aids the insertion or other movement of device 10 within the body. In some embodiments, the guide wire engaging member 65 is a hollow in device 10 extending from its distal end 16 to the manipulator 22 (as depicted in FIG. 1). In such an embodiment, plunger 20 would have a hollow, as would manipulator 22 and distal end 16.

Figure 5:
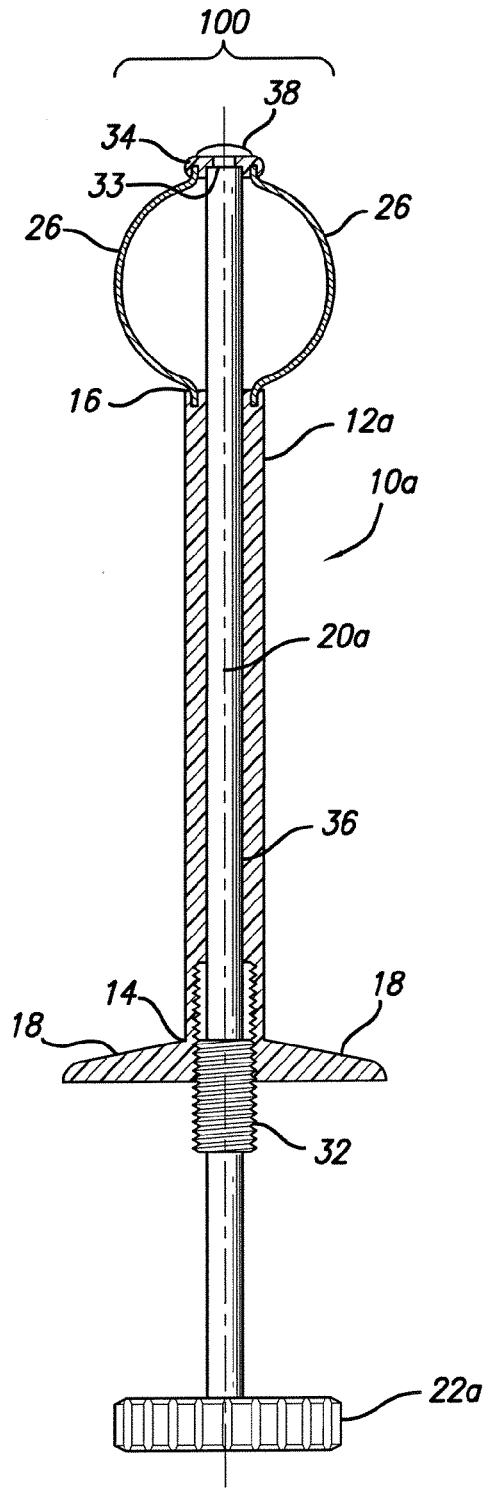
FIG. 5 is a partial cross-sectional view of the embodiment depicted in FIG. 4.
Figure 6:
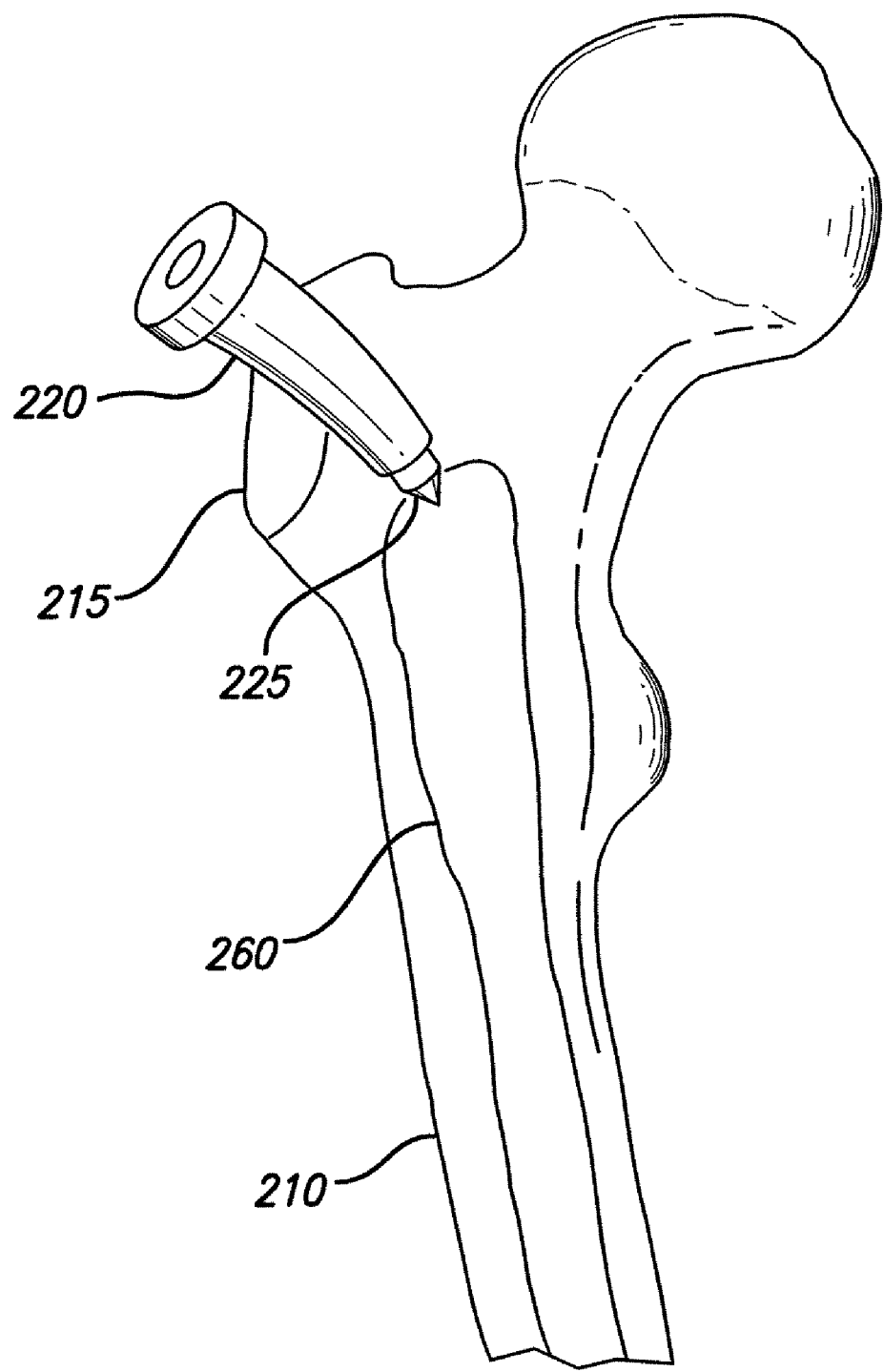
FIGS. 6-12 illustrate perspective views of the use of a device of the present invention used to perform a method of the present invention in which a long bone is treated.
Figure 7:
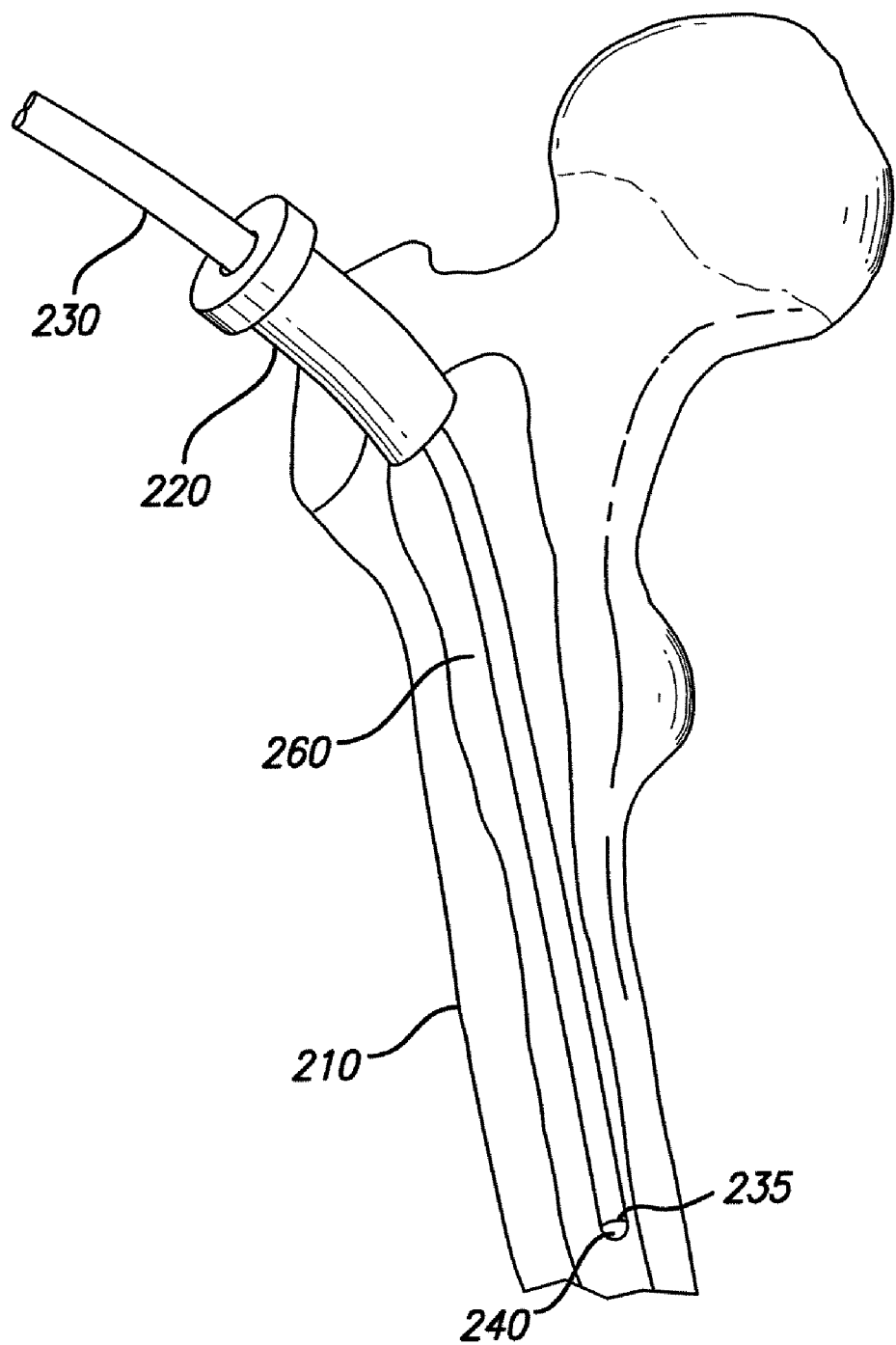
Figure 8:
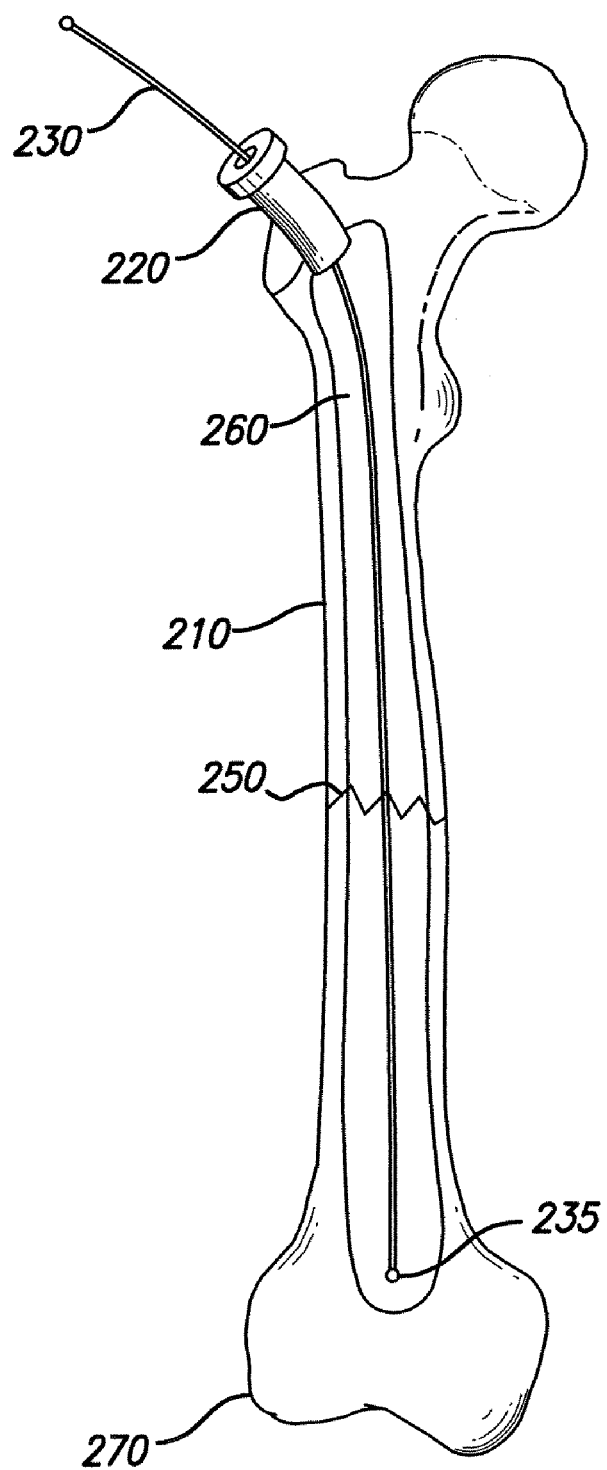
Figure 9:
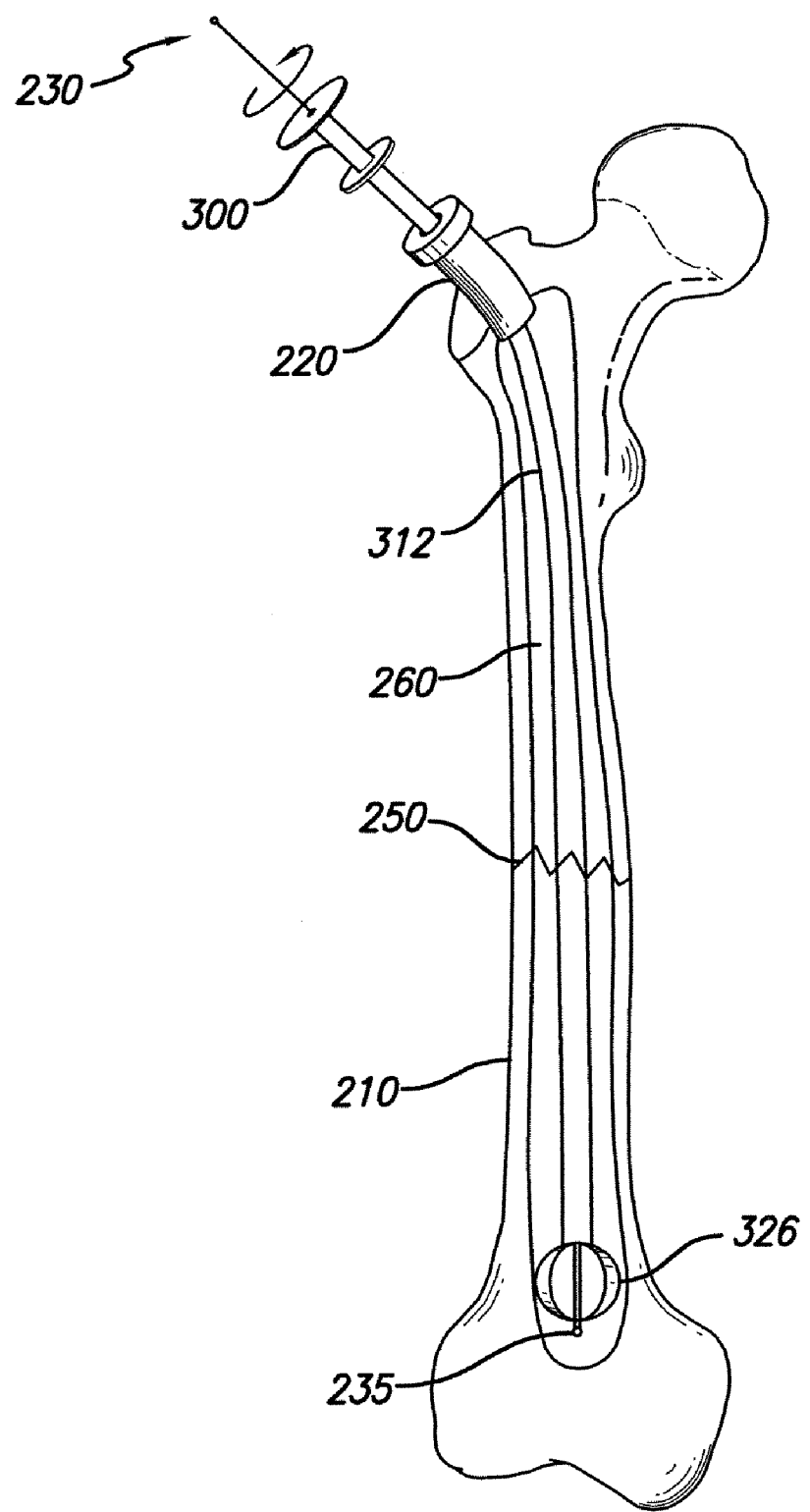
Figure 10:
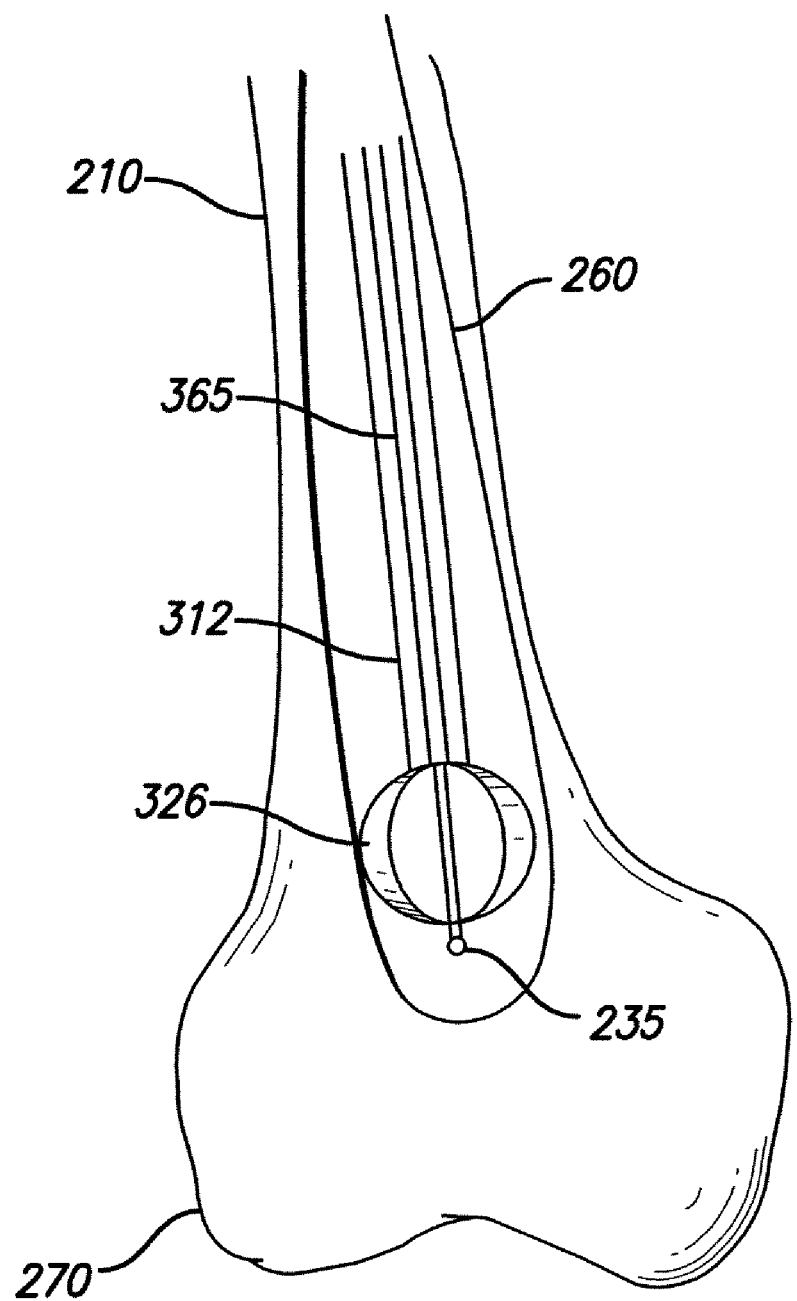
Figure 11:
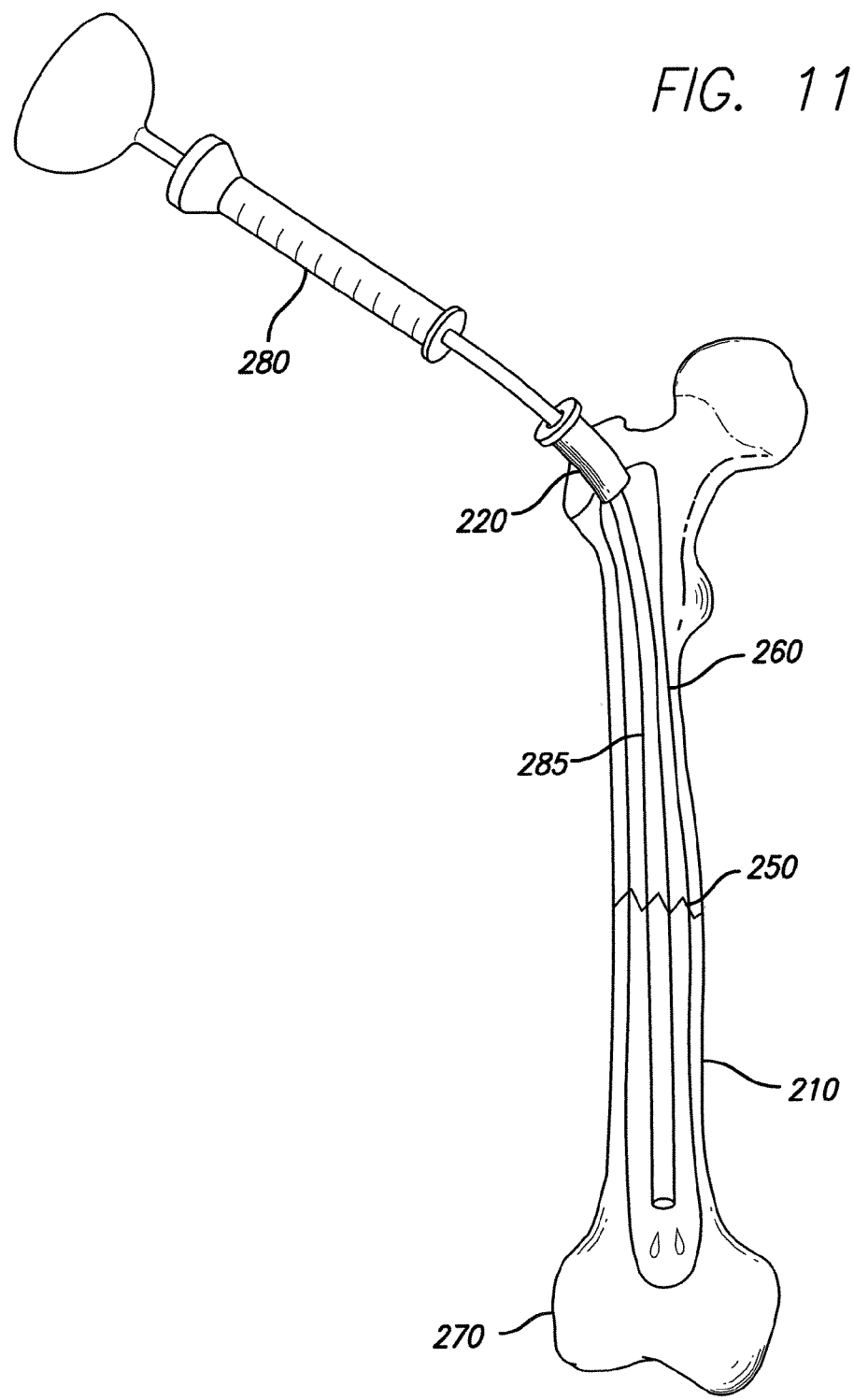
Figure 12:
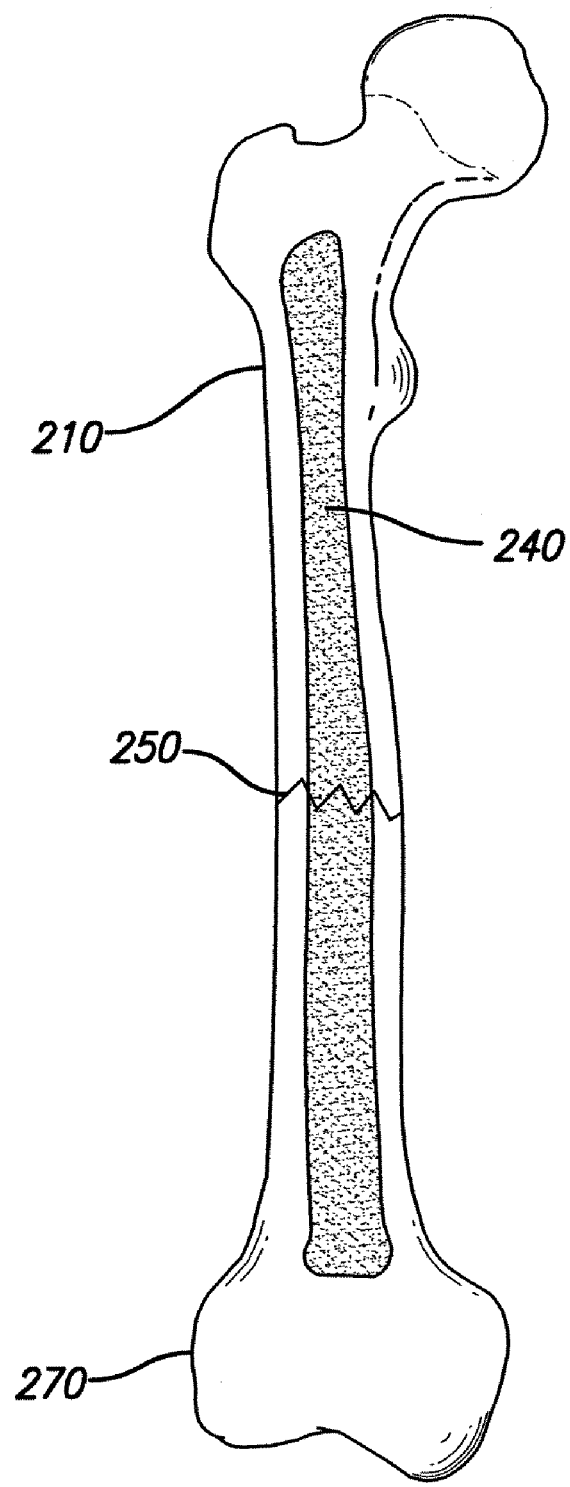

FIGS. 4 and 5 depict an alternative embodiment of a device of the present invention, device 10a. Similarly to the device 10 depicted in FIGS. 1 and 2, device 10a comprises a housing 12a having a proximal end 14 and a distal end 16, a grip member 18 (depicted as a pair of wings), lumen 13 and blades 26. Device 10a may also have guide wire engaging member 65 (as illustrated in FIG. 4). The depicted embodiment works in a manner similar to the embodiment depicted in FIGS. 1 and 2, but, among other differences, utilizes a manipulator 22a, housing 12a, and configuration of plunger 20a that are different than those in the embodiment depicted in FIGS. 1 and 2.

In the embodiment depicted in FIGS. 4 and 5, a proximal portion of the interior surface of the housing 12a has a threaded region 36. Similarly, a proximal portion of plunger 20a has a threaded region 32. The threaded portion 32 is threadably engaged to the internally threaded portion 36 of the housing 12a. As such, rotation of plunger 20a causes movement of plunger 20a along the axis of housing 12a. Housing 12a does not extend to the distal end of the device 10a in this embodiment. Distal end 16 is near the proximal end of blades 26. Blades 26 are attached at their proximal end to housing 12a and at their distal end to sleeve 34. Sleeve 34 is rotatably connected to plunger 20a is an annular sleeve 34 which partially resides within a continuous, circumferentially extending groove 33 which is disposed in close proximity to distal end 38 of plunger 20a. Sleeve 34 is capable of rotation relative to the screw unit 28 when the plunger 20a is rotated relative to the housing 12a.

Manipulator 22a in the depicted embodiment is a handle portion that extends radially from the axis of housing 12a. In this embodiment, manipulator 22a is configured to allow the user to grasp and rotate manipulator 22a and, thereby rotate plunger 20a. Of course, manipulator 22a can have any configuration capable of rotating plunger 20a relative to housing 12a. In the depicted embodiment, blades 26 are extended by counter-clockwise rotation of manipulator 22a which, in turn, causes counter-clockwise rotation of plunger 20a relative to housing 12a. In such an embodiment, the counter-clockwise rotation of manipulator 22a moves manipulator 22a away from the housing 12a, thereby causing plunger 20a to move proximally along the axis of housing 12a. Such movement decreases the distance between the distal end 16 of housing 12a and the distal end 38 of plunger 20a to decrease. Since the blades 26 are resilient and flexible and attached to the distal end 38 of plunger 20a and near the distal end 16 of housing 12a, this decrease in distance forces the blades 26 to expand or flex (and hence deploy) radially from the axis of housing 12a in the manner illustrated in FIG. 5. Conversely, in the depicted embodiment, when manipulator 22a and plunger 20a are rotated in a clockwise direction, the distance between the distal ends 16 and 38 is effectively increased, causing the blades 26 to return to the initial, unexpanded position illustrated in FIG. 4. Like in device 10, the blades 26 of device 10a may be partially expanded or deployed to a state lying anywhere between the extremes illustrated in FIGS. 4 and 5 by selective variation in the degree of rotation of manipulator 22a. Of course, one of skill in the art will appreciate that the device could be configured such that counter-clockwise movement contracts the blades 26 and clockwise movement expands the blades 26.

In some embodiments, the configuration of the screw mechanism is such that blades 26 will remain in a particular expanded state even though the user is not applying force to manipulator 22a. Accordingly, the blades 26 can be maintained in the deployed position without continuous application of force by the user and without the need for any ancillary clamping or similar device. In such embodiments blades 26 will remain until plunger 20a is rotated in a clockwise manner until the blades 26 are returned to their initial unexpanded position.

In those instances when the user wants to rotate device 10 in its entirety, the user may simultaneously rotate the housing 12a and plunger 20a. In another embodiment, such rotation may be assisted through the use of a clamp (not shown), or other fastening device or configuration operative to lock plunger 20a in place relative to the housing 12a. In this case, when the clamp is locked, device 10a may be rotated in its entirety by either rotating the plunger 20a (or manipulator 22a) or the housing 12a, without the user ensuring that the two are simultaneously rotating.

B. Methods of the Present Invention

In addition to the devices described above, the present invention also includes methods of using the devices of the present invention and any other suitable device.

A method of the present invention is used to treat and stabilize a fracture of a long bone or other hollow bone. An embodiment of such a method is depicted in FIGS. 6-12. As used herein, a long bone includes any bone that is longer than it is wide. Examples of long bone include, but are not limited to the femur, tibia, fibula, humerus, radius, ulna, and phalanges. The depicted embodiment involves the treatment of a femur fracture, but the methods may be applied to any long or hollow bone structure. As depicted, the method uses a device 300 that is similar to devices disclosed herein, but any suitable device may be used.

The method initially involves getting access to the marrow cavity 260 of long bone 210. In preferred embodiments access is gained percutanteously. In other embodiments, an open procedure may be used. In preferred embodiments, a cannula 220 is used to gain access to the interior volume of long bone 210. Cannula 220 may be made of any suitable material and should have a diameter sufficient to permit insertion of device 300. In some embodiments the cannula 220 may be a large bore curved cannula. In some embodiments, cannula 220 has a stylet 225 that may be used to cut or drill through the exterior surface of long bone 210 in order to gain access to the marrow cavity 260 of long bone 210. Access may be gained at any suitable part of the long bone 210. Preferably, in embodiments used for treating a femur, cannula 220 is inserted into the greatest trochanter 215. The cannula 220 is inserted until it reaches the marrow cavity 260 of long bone 210.

The extent of the insertion of cannula 200 may be determined by any suitable imaging technique. Generally, the extent of movement and the positioning of the various elements described (for example: percutaneous placement of the insertion cannula 220, passing of the guide wire 230, inserting device 300 and the delivery of the biological binding material) in the methods of the present invention is determined by any suitable imaging method. Preferably, a fluoroscopic imaging technique is used.

Once access to the marrow cavity 260 of long bone 210 is gained, guide wire 230 is inserted into the marrow cavity 260. Guide wire 230 may be made of any suitable material and may have any suitable gauge. In preferred embodiments, guide wire 230 has a small gauge. Guide wire 230 may have any suitable flexibility. In preferred embodiments, guide wire 230 includes a moderate flexibility. In preferred embodiments, guide wire 230 has a stop 235. In some embodiments, stop 235 may limit the movement of device 300 by stopping device 300. In some embodiments stop 235 may function to anchor guide wire 230 within marrow cavity 260. In some embodiments, stop 235 comprises a bead-like structure. Once inserted, guide wire 230 is advanced toward the distal end 270 of long bone 210. The guide wire 230 is passed distally past the fracture site 250 and positioned toward the distal end 270 of long bone 210.

At some point during or before beginning the procedure, a reduction of the fracture is performed by any suitable method. In some embodiments, the fracture reduction may be an open reduction. In other embodiments, the fracture reduction may be a closed reduction. In preferred embodiments, the fracture reduction is performed before the guide wire 230 is advanced past the fracture site 250. In some embodiments, a splint or other external stabilizing structure is used to maintain the reduction of the fracture. In preferred embodiments, the splinting/stabilizing may be done after the guide wire 230 is advanced past the fracture site.

Device 300 is inserted into the marrow cavity 260 of long bone 210. In some embodiments, device 300 may be inserted after the reduction of the fracture. In some embodiments, device 300 may be inserted after guide wire 230 is advanced as far distally as may be desired. Preferably, device 300 is inserted after the reduction of the fracture and after guide wire 230 has been advance to the desired position. In preferred embodiments, device 300 includes a plurality of blades 326, a guide wire engaging member 365 (depicted in FIG. 10 as a hollow in the center of the device 300), a manipulator 322, and a housing 312. In such preferred embodiments, these elements are similar to blades 26, guide wire engaging member 65, manipulator 22a and housing 12a described with respect to the devices of the present invention.

In the depicted embodiments, device 300 is inserted over the guide wire 230 such that guide wire 230 passes into guide wire engaging member 365 and directs device 300 along guide wire 230 and toward the distal end 270 of long bone 210. Device 300 may be advanced distally until it reaches a desired position. In preferred embodiments, device 300 may be advanced past the fracture site 250 and until it reaches stop 235 on guide wire 230. In preferred embodiments, device 300 is advanced with blades 326 in a retracted position (e.g., similar to the position of blades 26 in FIGS. 1 and 4). Positioning of device 300 may be determined by tactile feel, imaging, or any other suitable method. Preferably, tactile feel and/or fluoroscopic imaging techniques are used.

Once device 300 has reached its desired position, blades 326 are radially expanded to a desired diameter by application of force to manipulator 322. In the deployed position the device is both rotated around the axis of the housing and moved proximally (i.e. away from the distal end 270 of long bone 210). Consequently blades 326 produce an internal osteotomy along the length of the trabecular bone within the marrow space. In some embodiments, the osteotomy process may be repeated one or more times. In some embodiments, the osteotomy may be performed as device 300 is moved distally toward the distal end 270 of long bone 210. Once the osteotomy process is complete, device 300 is removed from marrow cavity 260 of long bone 210. In preferred embodiments, blades 326 are returned to an unexpanded state prior to removal of device 300 from marrow cavity 260 of long bone 210.

Once the osteotomy is complete, a biological binding material is delivered to marrow cavity 260 of long bone 210. Preferably, a cement containing PMM is used. In some embodiments, the biological binding material also includes barium. The biological binding material may be instilled into the marrow cavity 260 of long bone 210 by any suitable method. In a preferred embodiment, the biological binding material is instilled using a device having a calibrated barrel 280 that may measure the volume of the material being instilled. In preferred embodiments, calibrated barrel 280 is attached to a delivery tube 285 that is passed over the guide wire 230 still in marrow cavity 260. Delivery tube 285 may be made of any suitable material. Preferably, delivery tube 285 is inserted until it reaches the end of guide wire 230, near the distal end 270 of long bone 210. In some embodiments, guide wire 230 is removed once delivery tube 285 has reached the desired position.

Biological binding material 290 is instilled to the desired level, generally an amount sufficient to span the fracture site 250 both distally and proximally. In some embodiments, biological binding material 290 is instilled until marrow cavity 260 is substantially full. In preferred embodiments, biological binding material 290 is instilled until marrow cavity 260 is substantially completely full. In some embodiments, biological binding material 290 is instilled in a manner that ensures a substantially continuous internal cast of the marrow cavity 260 without any substantial gaps or interruptions. In certain embodiments, delivery tube 285 is removed gradually as the biological binding material 290 is added. Any suitable imaging technique may be employed to monitor the amount of biological binding material 290 in marrow cavity 260. In preferred embodiments, continuous fluoroscopic-imaging is used to monitor the deposition of the biological binding material 290 within marrow cavity 260, including determining if there is undesired extravasation of the biological binding material out of the fracture site 250. Once the biological binding material 290 is instilled, all equipment is removed, including cannula 220 and delivery tube 285. By allowing trabecular bone to remain, the injected PMM cement can interdigitate and better adhere to the internal bone structure. Consequently, the PMM cement forms a well-adhered strut within the fractured long bone that will be able support the fracture reduction. If the trabecular bone is completely reamed and a smooth internal cortical bone surface remains, the PMM cement may not sufficiently adhere to the internal cortical bone to resist cement/bone separation when subject to high internal stress forces with activity.

Once the method is complete, the long bone 210 should be inspected by any suitable method and the limb (or other relevant body part) should be splinted or otherwise immobilized to ensure that the fracture reduction is not lost while the biological binding material 290 is hardening. Once the biological binding material 290 has hardened the limb or other structure should have added stability in multiple planes of stress including compression and torsion. Post operatively the patient may be managed in a similar fashion to that of a patient that has had a intramedullary rod inserted into a long bone.

It is seen that devices and methods are provided. One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in this description may practice the invention as well.

While various embodiments of the present invention have been described above, it should be understood that they have been presented by way of example only, and not of limitation. Likewise, the various diagrams may depict an example configuration for the invention, which is done to aid in understanding the features and functionality that may be included in the invention. The invention is not restricted to the illustrated example configurations, but the desired features may be implemented using a variety of alternative configurations. Indeed, it will be apparent to one of skill in the art how alternative functional or physical configurations may be implemented to implement the desired features of the present invention. Additionally, with regard to operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary illustrations and figures. As will become apparent to one of ordinary skill in the art after reading this document, the illustrated embodiments and their various alternatives may be implemented without confinement to the illustrated examples.

The invention claimed is:

1. A method of adding stability to a long bone comprising the steps of:
    accessing the marrow cavity of the long bone;
    inserting a device into the marrow cavity, wherein the device has a plunger with a blade parallel to the axis of the plunger;
    reducing the volume of trabecular bone within the marrow cavity by bending the blade convexially from an axis of the plunger while rotating the blade about the
    axis of the plunger using a threaded track between the plunger of the device and a housing of the device, thereby cutting an ovoid path through the trabecular bone, wherein a proximal end of the blade is coupled to a distal end of the plunger of the device, and a distal end of the blade is coupled to the housing of the device; and
    instilling a biological binding material into the marrow cavity of the long bone, wherein
    the amount of the biological binding material instilled is sufficient to add stability to the long bone.

2. The method of claim 1, wherein the accessing step comprises a percutaneous method.

3. The method of claim 1, wherein the variable diameter cutting element comprises a plurality of blades.

4. The method of claim 3, wherein the reducing step comprises manipulating the plurality of blades to cut trabecular bone within the marrow cavity to create a space in the marrow cavity.

5. The method of claim 1, wherein the biological binding material is PMM cement.

6. The method of claim 1, wherein the biological binding material interdigitates with trabecular bone in the marrow cavity.

7. The method of claim 1, further comprising the step of monitoring the movement of the device by fluoroscopic imaging.

8. The method of claim 1, wherein the step of reducing the volume of trabecular bone within the marrow cavity further comprises activating a single manipulator to both bend the blade and rotate the blade about the axis of the plunger.

9. The method of claim 8, wherein the step of activating the single manipulator comprises rotating a threaded manipulator.

10. The method of claim 1, wherein the manipulator bends the blade while rotating the blade about the axis of the plunger.

* * * * *